US012691261B2

(12) United States Patent
Ponten et al.

(10) Patent No.: US 12,691,261 B2
(45) Date of Patent: Jul. 28, 2026

(54) BALLOON CATHETER SYRINGE FOR OBTAINING NOMINAL INFLATION PRESSURE AND DEFLATION VACUUM

(71) Applicant: GYRUS ACMI, INC., Westborough, MA (US)

(72) Inventors: Ryan Ponten, Redmond, WA (US); Jean-Martin Baillargeon, Edmonds, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 812 days.

(21) Appl. No.: 18/048,826

(22) Filed: Oct. 21, 2022

(65) Prior Publication Data

US 2023/0173234 A1     Jun. 8, 2023

Related U.S. Application Data

(60) Provisional application No. 63/270,810, filed on Oct. 22, 2021.

(51) Int. Cl.
*A61M 25/10*          (2013.01)

(52) U.S. Cl.
CPC ............................. *A61M 25/10182* (2013.11)

(58) Field of Classification Search
CPC ...... A61M 25/10187; A61M 25/10188; A61M 25/1018; A61M 25/10181; A61M 25/10182; A61M 2205/6081; A61M 2205/583; A61M 2205/582; A61M 2205/584

See application file for complete search history.

(56) References Cited

U.S. PATENT DOCUMENTS

| | | | | |
|---|---|---|---|---|
| 5,817,001 A | * | 10/1998 | Leschinsky | ......... A61M 60/139 |
| | | | | 600/18 |
| 6,217,558 B1 | * | 4/2001 | Zadini | .............. A61B 5/150244 |
| | | | | 604/164.01 |
| 9,937,330 B2 | | 4/2018 | Schaeffer | |
| 2004/0019323 A1 | | 1/2004 | Carter | |
| 2008/0172041 A1 | * | 7/2008 | Shehata | ................ A61M 25/04 |
| | | | | 604/544 |
| 2017/0043139 A1 | * | 2/2017 | Root | ............... A61M 25/10184 |

FOREIGN PATENT DOCUMENTS

| | | | | |
|---|---|---|---|---|
| EP | 2801387 A1 | * | 11/2014 | ........... A61F 2/2496 |
| WO | WO-03090836 A1 | * | 11/2003 | ...... A61M 25/10182 |

* cited by examiner

*Primary Examiner* — Rebecca E Eisenberg
(74) *Attorney, Agent, or Firm* — Schwegman Lundberg & Woessner, P.A.

(57) ABSTRACT

Various aspects of methods, systems, and use cases may be used to inflate a balloon catheter using a syringe. The syringe may include a channel portion shaped to create a channel, and a plunger, for example including an inserted end and a free end, which when inserted in the channel to place the inserted end at a plunger starting position, causes a starting pressure to be applied to the balloon catheter. In an example, the channel portion or the plunger includes at least one visual indicia indicating the plunger starting position, the plunger starting position located along an insertion axis (e.g., of the channel portion and the plunger).

18 Claims, 6 Drawing Sheets

200

202 — PREPARE BALLOON CATHETER AND SYRINGE

204 — INSERT BALLOON CATHETER INTO PASSAGEWAY

206 — INFLATE BALLOON OF BALLOON CATHETER

208 — CONFIRM SIZING OF BALLOON IN PASSAGEWAY

210 — DEFLATE BALLOON OF BALLOON CATHETER

212 — CONFIRM TANG PLACEMENT

BALLOON CATHETER SYRINGE FOR OBTAINING NOMINAL INFLATION PRESSURE AND DEFLATION VACUUM

CROSS-REFERENCE TO RELATED APPLICATIONS

This non-provisional patent application claims priority to and the benefit of the filing of U.S. Provisional Patent Application Ser. No. 63/270,810, filed on Oct. 22, 2021, entitled "BALLOON CATHETER SYRINGE FOR OBTAINING NOMINAL INFLATION PRESSURE AND DEFLATION VACUUM", and the specification, claims, and figures thereof are hereby incorporated by reference herein in its entirety.

BACKGROUND

Endoluminal valves may be placed inside airways leading to a diseased portion of a lung. The endoluminal valves redirect breathed air away from diseased areas toward healthier portions of the lung. The endoluminal valves can be check valves that allow air and bodily fluids (e.g., mucus) to escape the diseased portions of the lung while preventing breathed air from entering these portions. Diseased portions of the lungs may include lung areas with significant emphysema. Diseased portions of a lung tend to increase in volume (e.g., lung hyperinflation) and prevent other healthier portions from adequately expanding. Endoluminal valve placement can be an effective treatment for reducing the volume occupied by diseased lung portions, which do not significantly contribute towards the $O_2$—$CO_2$ gas exchange. Reducing the volume of diseased portions provides healthy lung portions with more space to fully inflate during the respiratory cycle, which allows for markedly greater gas exchange.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
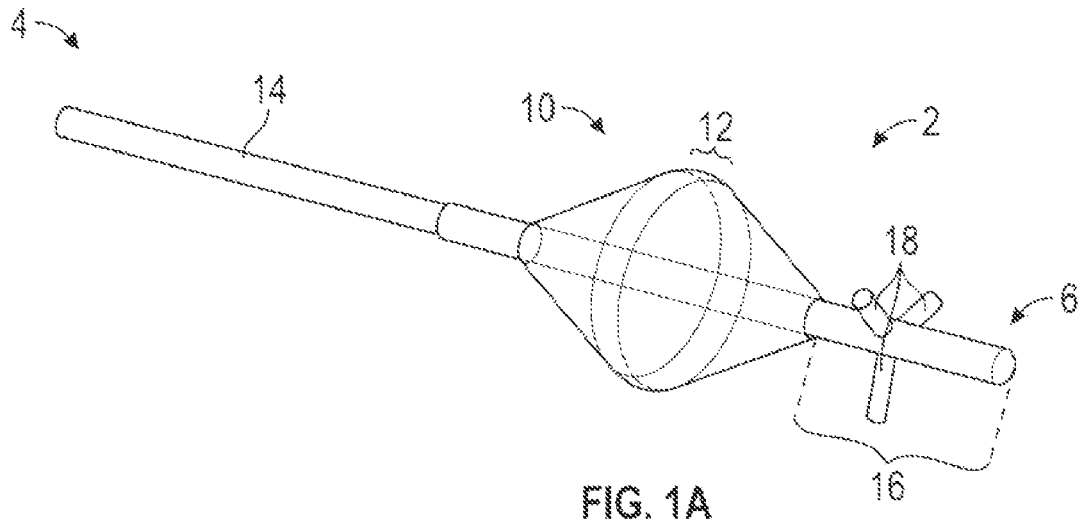
FIG. 1A illustrates aspects of a balloon catheter.

Before placing an endoluminal valve, clinicians may perform various planning procedures to select an appropriate location for valve placement and to determine an appropriate valve size. This may include delivering a balloon catheter to a target location within a patient's passageway, such as an airway. At the target location, a sizing balloon can be expanded via inflation to facilitate visual confirmation (e.g., via an endoscope video feed) that both: (i) the sizing balloon of a known nominal size matches the passageway diameter at the target location; and (ii) that tangs indicate that placement of a valve at the target location will result in valve anchors engaging the passageway wall. To determine whether the size is appropriate, the sizing balloon on the balloon catheter may be inflated by applying a positive pressure.

As described in more detail below in relation to FIGS. 2A and 2B, after having inflated the sizing balloon, a clinician's view of anything distal from the balloon (including the anchor tangs described below) may be obscured due to the balloon not fully deflating when at a neutral (e.g., atmospheric) pressure. For example, the balloon may obscure or block the clinician's view of the tangs at the distal side of the balloon. In occlusion balloons, which lack elasticity (e.g., non-compliant balloons), the problem of the balloon not fully deflating may be exacerbated. For the clinician to see the tangs, the balloon may need to be actively deflated by applying an amount of negative pressure (e.g., vacuum) to the balloon.

As an additional difficulty, if the plunger is not precisely aligned at a neutral position before connecting the syringe to a balloon catheter, there is risk of under-inflation or over-inflation, which leads to balloon outer diameter variation. As the inflated balloon is used by the clinician as a reference for visual confirmation of the size of the target location within the patient's airway, any deviation of the outer diameter of the inflated balloon from an intended nominal diameter is highly undesirable. Aligning the plunger at a neutral position prior to connecting the syringe to the balloon catheter ensures that depressing the plunger displaces a known volume of fluid (e.g., air) and achieves an intended internal pressure within the inflated balloon.

Under one approach, the balloon catheter is inflated using a syringe that is bottomed out, or fully retracted within a channel of the syringe, when the catheter is attached. This bottoming out of the plunger provides a positive stop to ensure the plunger is precisely aligned at the appropriate neutral location when the balloon catheter is connected to the syringe in order to ensure inflation to the proper nominal internal pressure.

The balloon catheter may be used to measure one or more cross-sectional dimensions of a structure. The balloon catheter may measure one or more diameters of a structure. The structure may be a passageway such as an airway. The balloon catheter may measure a plurality of cross-sectional dimensions (e.g., diameter) of a passageway. In some embodiments, the balloon catheter measures a passageway to determine which size of valve can be used to seal the passageway. For example, the passageway may measure a dimension of a passageway from one side to the other despite the passageway possibly being non-circular or irregular in shape. If the passageway is circular, then the cross-sectional dimension is a diameter. The balloon catheter may be used to measure an axial length of a passageway. The balloon catheter may be used to measure if there are any obstructions within a given axial length that would affect a valve from deploying, from being retained in a location, from sealing, or a combination thereof. The balloon catheter may allow a user to concurrently measure one or more cross-sectional dimensions and one or more axial lengths of a passageway. The axial length is a length of the valve or balloon catheter from a distal end to a proximal end. The axial length may be a distance that the valve spans when retracted, deployed, or both.

To view the balloon catheter, including the balloon and tangs, an imaging device, such as an endoscope, may be used. However, the tangs may not be visible when the balloon is inflated or at a neutral pressure. For example, the balloon may be a non-compliant balloon such that in a neutral pressure, the balloon obstructs the view distal to the balloon. A syringe may be used to apply a negative, or deflation, pressure to the balloon catheter, thereby deflating the balloon. The syringe may also be used to apply a positive, or inflation, pressure to the balloon catheter, thereby inflating the balloon. To enable the syringe to provide both a negative pressure and a positive pressure, the syringe may be attached to the balloon catheter when the plunger is at a mid-span neutral position (e.g., a mid-span "zero") that is partway within the channel (i.e., between two extreme positions of the plunger). Accordingly, the plunger can be pushed into the channel to create a positive pressure and withdrawn within the channel to create a negative pressure. The syringe may include one or more visual indicia to aid a user with positioning the plunger in the correct location to deliver the various pressures. The visual indicia may be on the channel portion of the syringe or may be on the stem of the plunger of the syringe, or both of these.

The above discussion is intended to provide an overview of subject matter of the present patent application. It is not intended to provide an exclusive or exhaustive explanation of the invention. The description below is included to provide further information about the present patent application.

FIG. 1A illustrates aspects of a balloon catheter 2. The balloon catheter 2 in a retracted state may fit within a delivery device, such as a delivery catheter, a sheath, or a channel of a bronchoscope. The balloon catheter 2 includes a stem 14 with a distal end 6 and a proximal end 4. The stem 14 may be rigid. The stem 14 may be flexible. The stem 14 may be solid. The stem 14 may be hollow. The stem 14 may be made of plastic, metal, a bio-compatible material, or a combination thereof. The stem 14 may have one or more components that extend through the stem. The stem 14 may be used to move (e.g., push) the balloon catheter 2 into place. The stem 14 may be used to move (e.g., pull) the balloon catheter 2 out of the passageway. The stem 14 may include one or more fluid conduits such as can extend from the proximal end 4 to the distal end 6. The stem 14 may include one or more actuator devices (e.g., wires, strings, cables) that may extend through a length of the stem 14. The stem 14 may include one or more fluid conduits that extend through the stem 14 and into a balloon on the balloon catheter 2.

The distal end 6 of the stem 14 includes an anchor indicator 16, such as with a plurality of tangs 18. The plurality of tangs 18 may be expandable and retractable. For example, the tangs 18 may have a molded structure that is biased into an expanded configuration in which the tangs protrude radially from the stem 14, but that may be compressed into a folded configuration in which the tangs 18 lay flat against the stem 14. In this way, upon the balloon catheter 2 being extended out of a working channel of a delivery device (e.g., a bronchoscope), the tangs 18 may spring into the expanded configuration. Then, upon the balloon catheter 2 being retracted back into the working channel of the delivery device (e.g., bronchoscope), the tangs 18 may be forcibly returned back to the folded configuration. The distal end 6 may be located the farthest into a passageway. The distal end 6 may extend beyond a location of where a distal end 6 of a valve may extend (e.g., a length indicator of the anchor indicator 16 may extend distal of the tangs 18).

The proximal end 4 may be located opposite the distal end 6. The proximal end 4 may be an end of the balloon catheter 2 closest to a user, an opening of a passageway, or both. A stem 14 may extend from the proximal end 4 to the distal end 6.

The balloon 10 is located between the distal end 6 and the proximal end 4 and is proximal of the anchor indicator 16. The balloon 10 may be a non-compliant balloon. The balloon 10 is inflatable and deflatable. When inflated, balloon 10 indicates the maximum airway size that a valve (shown in FIG. 1B) can occlude/seal. The balloon 10 may include a seal area indicator 12 that represents a contact location of a valve (shown in FIG. 1B).

The balloon 10 may have a shape that is spherical, egg shaped, one or more cones, one or more pyramids, one or more pentagons, diamond shape, oval, round shaped, kite shaped, two back-to-back pyramids, or a combination thereof. The balloon 10, in the deployed state (e.g., an inflated state), may have a location along the length of the balloon where the diameter of the balloon 10 is farthest from the stem 14. The diameter of the balloon 10, in the deployed state (e.g., an inflated state), may gradually increase in distance from the stem, gradually decrease in distance from the stem 14, or both. The balloon 10 may have one or more segments that run parallel to the stem 14. The balloon 10 may be two back-to-back shapes. For example, the balloon 10 may be two cones that are back-to-back with a linear segment connecting the cones. The linear segment may be the seal area indicator 16.

The balloon 10 is expandable and contractible. The balloon 10 may have a portion that moves along the length of the stem 14. The balloon 10 may be manipulated by an actuator device. The balloon 10 may be manipulated by an actuator device that extends through the stem 14. The balloon 10 may be fixedly connected to the stem 14. The balloon 10 may be elastically deformable. The balloon 10 may not be elastically deformable (i.e., the balloon 10 may only expand to a predetermined size). The balloon 10 may conform to non-round shapes. The balloon 10 may be made of a non-compliant material or a semi-compliant material. The balloon 10, in the deployed state, may be made of polyethylene terephthalate, polyester, a thermoplastic, polypropylene, polyether, a polyether block amide, polyamide, polyester, polyurethane, a minimally-stretchable plastic, a minimally-stretchable biocompatible plastic, a non-elastic plastic, a non-stretchable plastic, or a combination thereof. The balloon 10 may be deployed using any fluid. The balloon 10 may be deployed using a compressible fluid (e.g., air) or a non-compressible fluid (e.g., saline).

The balloon catheter 2 may have a dimension (i.e., a length) that is greater than a distance that a delivery catheter (e.g., bronchoscope) extends into a passageway so that the balloon catheter 2 can extend out of a working channel of the delivery catheter past the distal end of the delivery catheter. The balloon catheter 2 may have dimensions that simulate or otherwise correspond to those of a valve. The balloon catheter 2 may have a length of about 8 mm or more, about 10 mm or more, about 11 mm or more, about 12 mm or more when measured from the seal area indicator 12 to the tangs 18. The balloon catheter 2 may have a length of about 20 mm or less, about 15 mm or less, or about 13 mm or less. The balloon catheter 2 may be compressed (in a retracted state) to fit within the bronchoscope and may expand (in a deployed state) to substantially fill a length of a passageway such as an airway or a branch of bronchia or a bronchiole.

The deployed state may have the balloon 10 partially or fully inflated. The deployed state may have the plurality of tangs 18 extending radially outward from the stem 14, such as orthogonally thereto. The deployed state may have all of the plurality of tangs 18 extending radially outward from the stem 14 and may have the balloon 10 inflated so that the balloon 10 is substantially in contact with a wall of a passageway. The balloon catheter 2 may be moved from the deployed state back into the retracted state so that the balloon catheter 2 may be removed. The balloon catheter 2 may be retracted from the proximal end 4 to the distal end 6.

The seal area indicator 12 may have a length that is substantially the same as an area to be sealed by a valve. The cross-sectional dimension of the seal area indicator 12 of the balloon catheter 2 may be substantially identical to the cross-sectional dimension of the valve (i.e., the difference may be about 1 mm or less, about 0.5 mm or less, or about 0.25 mm or less). The seal area indicator 12 of the balloon catheter 2 may have a maximum diameter ($D_1$). The seal area indicator 12 of the balloon catheter 2 may indicate how the valve will seal a non-round shape, an irregular shape, or both. The seal area indicator 12 of the balloon catheter 2 may indicate how a range of cross-sectional dimensions will seal. The seal area indicator 12 may be at a proximal end of the balloon 10, indicate a proximal end of a valve, or both. The seal area indicator 12 of the balloon catheter 2 may indicate a maximum size (e.g., diameter) that a valve can seal. The seal area indicator 12 of the balloon catheter may have a largest cross-sectional dimension of about 4 mm or more, about 5 mm or more, about 6 mm or more, about 7 mm or more, or about 9 mm or more. The seal area indicator 12 of the balloon catheter may have a largest cross sectional length of about 12 mm or less or about 10 mm or less. The seal area indicator 12 may be used in conjunction with the anchor indicator 16 to determine the best size valve to use for a site of a passageway.

The anchor indicator 16 may function to determine if the anchors of the valve can open. The anchor indicator 16 may function to measure a minimum size passageway that a valve may seal. The anchor indicator 16 may function to measure both the minimum size and maximum size a valve can be sealed. The anchor indicator 16 may function to measure a maximize size valve that the valve can seal. The anchor indicator 16 may function to measure the passageway for a maximum cross-sectional dimension of next size down or a minimum cross-sectional dimension of a next size up valve relative to the cross-sectional dimension being measured using the balloon 10. The anchor indicator 16 may have a cross-sectional dimension of about 6 mm or more, about 8 mm or more, about 9 mm or more, about 10 mm or more, or about 11 mm or more. The anchor indicator 16 may have a cross-sectional dimension of about 20 mm or less, about 18 mm or less, about 15 mm or less, about 13 mm or less, or about 12 mm or less. The anchor indicator 16 may function to measure an axial length that a delivery catheter may extend into a passageway. The anchor indicator 16 may have a portion that extends distal beyond the plurality of tangs 18 (i.e., a length indicator). The length indicator 20 may extend beyond the plurality of tangs 18. The length indicator 20 may extend beyond the location of the anchors of the valve, in the deployed state, so that the anchor indicator 16 indicates the distance (e.g., axial length): the valve delivery catheter extends beyond the end of the valve during deployment, the length of the anchors when extended distally, or both. The length indicator 20 may indicate the length of the valve in the deployed state. The length indicator 20 may indicate the length of the valve in the retracted state. The anchor indicator may indicate a total length of the valve plus a delivery catheter during deployment. A length of the balloon catheter 2 from the seal area indicator 12 to the distal end of the anchor indicator 16 is equal to the length of valve plus the length of a delivery catheter needed to deploy the valve. The length of the length indicator distally beyond the plurality of tangs 18 may be about 1 mm or more, about 2 mm or more, or about 3 mm or more. The length of length indicator beyond the plurality of tangs 18 may be about 10 mm or less, about 8 mm or less, or about 5 mm or less.

When in the expanded configuration in which the tangs 18 protrude radially from the stem 14, the anchor indicator 16 may provide a visual reference for a clinician to visually confirm both a placement at which valve anchors will reside in relation to the seal indicator area 12 and that the valve anchors will be sufficiently sized to contact the airway wall (thereby securing the endoluminal valve in place). The tangs 18 may function to measure a minimum passageway that a valve can seal. The tangs 18 may function to measure a maximum passageway that a valve can seal. The tangs 18 may extend radially outward from the stem 14. The tangs 18 may all be the same length. The length of the tangs 18 may vary. For example, some tangs 18 may have a length that is equal to a minimum size (minor tangs) that a valve can seal and other tangs may have a length that is equal to a maximum size (major tangs) that a valve can seal. The balloon catheter 2 may have two or more tangs 18, three or more tangs 18, four or more tangs 18, or even five or more tangs 18. The balloon catheter 2 may have one or more minor tangs or two or more minor tangs. The balloon catheter 2 may have one or more major tangs or two or more major tangs. The minor tangs and the major tangs may be located an angle apart from each other. The major tangs and minor tangs; two major tangs, two minor tangs; or a combination of major tangs and minor tangs may be located apart by about 180 degrees or less, about 135 degrees or less, about 120 degrees or less, or even about 105 degrees or less (e.g., each of the tangs 18 may be located about 90 degrees apart when there are four tangs). The major tangs and minor tangs; two major tangs, two minor tangs; or a combination of major tangs and minor tangs may be located apart by about 25 degrees or more, about 45 degrees or more, or about 75 degrees or more. The tangs 18 may have a length that serves as a visual indication as to whether the valve anchors, upon opening (e.g., expanding) will contact the airway wall so as to secure the endoluminal valve in place within the target area. The tangs 18 may have a length that indicates if the valve anchors can contact the passageway. The one or more tangs 18 may be static (i.e., open in the retracted state). The one or more tangs 18 may be resilient so that the tangs 18 move to an open or free state. A length of the balloon catheter 2 from the tangs 18 to the seal area indicator 12 may indicate the length of the valve. The tangs 18 placement may be used to measure one or more lengths in a passageway.

Figure 1B:
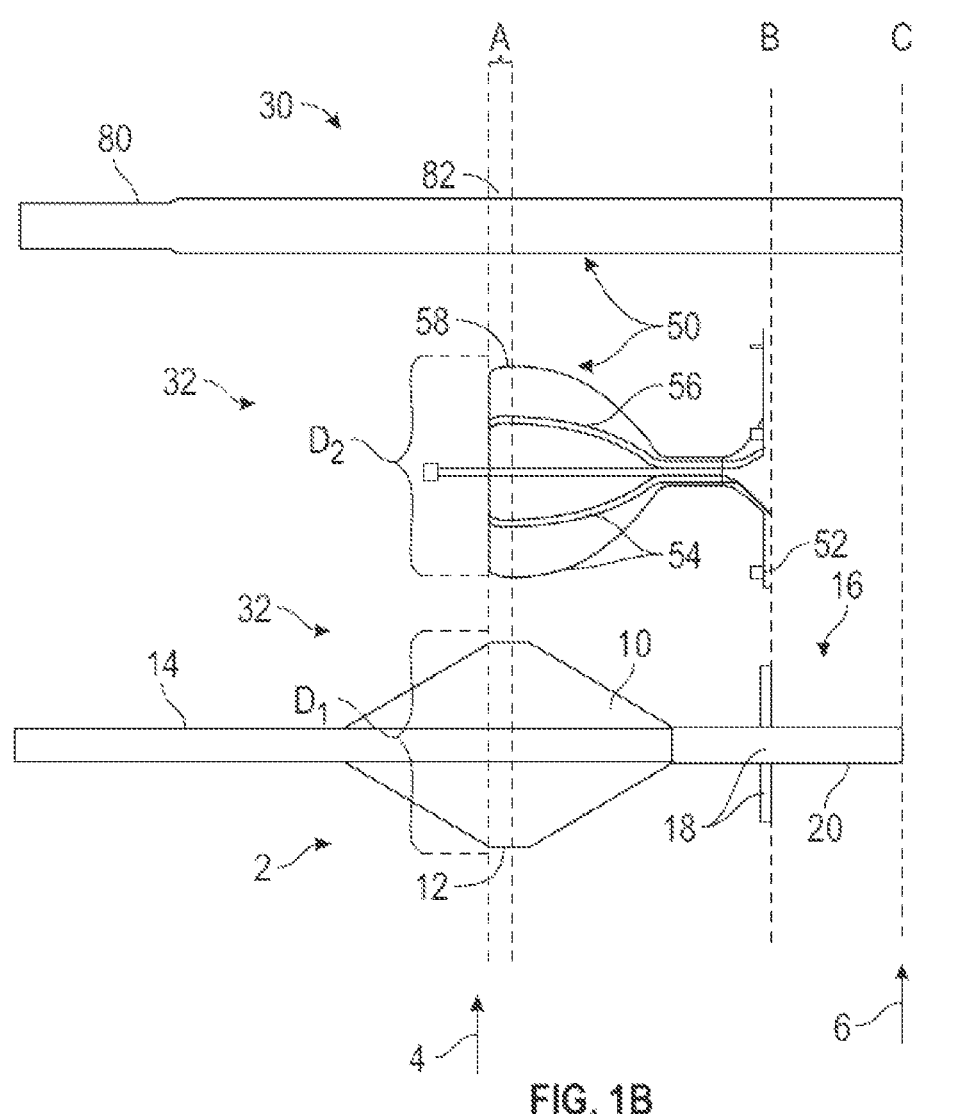
FIG. 1B illustrates a comparison of the balloon catheter and an endoluminal valve in a retracted and deployed state.

FIG. 1B illustrates (1) the balloon catheter 2 in a deployed state 32 that is aligned with (2) a valve 50 in the deployed state 32 to demonstrate the features that the balloon catheter 2 are simulating and (3) a valve 50 in the retracted state 30 (inside the valve delivery catheter). The valve 50 includes a seal area 58 at a proximal end of struts 54 and membrane 56 that define the shape of the valve 50 in a deployed state. The valve 50 includes anchors 52 to affix the valve 50 in a passageway, such as an airway (not shown). The valve 50 may be a check valve. The valve 50 may be an endoluminal valve.

The delivery catheter 80 includes a seal area indicator 82 to aid in positioning the delivery catheter for deployment of the valve 50. The seal area indicator 12 of balloon catheter 2 measures a passageway (not shown) so that the seal area indicator 12 indicates if a seal area 58 of the valve 50 in the deployed state 32 will seal the passageway. The seal area indicator 12 also indicates where the seal area 58 of the valve 50 will longitudinally align in both the retracted state 30 and the deployed state 32. The seal area indicator 82 of the delivery catheter 80 assists a user in longitudinally aligning the valve 50 with the area to be sealed which is indicated by the lines (A). While aligned, the valve 50 is deployed by the balloon catheter 2 such that the seal area 58 is maintained within the lines (A) (i.e., the delivery catheter 80 is retracted while the valve 50 does not change position). The seal area indicator 12 of the balloon catheter 2, when inflated, has a diameter (D1) that is larger than the diameter (D2) of the area 58 of the deployed valve 50 by a small offset to ensure that the valve 50 can seal an airway (not shown) when the valve is fully deployed. The seal area indicator 12 indicates a proximal end of the valve 50 although the balloon catheter 2 has some balloon 10 that extends beyond the seal area indicator 12. The balloon 10 of the balloon catheter 2 tapers downward towards the stem 14 so that the balloon 10 generally mirrors the shape of the struts 54 and membrane 56.

The tangs 18 of anchor indicator 16 of balloon catheter 2 provide a visual depth marker to indicate the area in the airway (not shown) the anchors 52 of the valve 50 can open and will contact the walls of the airway when the seal area 58 of the valve 50 is aligned with the seal area indicator 12 of the balloon catheter 12. The tangs 18 represent the minimum size that the seal area 58 of the valve 50 can seal. The tangs 18 align with the anchors 52 in the deployed state along line (B) as is shown. The anchor indicator 16 has a length indicator 20 that extends distal of the tangs 18 that represents the approximate swing of the anchors 52 to ensure that the anchors 52 can deploy and to ensure that the delivery catheter 80 can fully extend into the passageway (not shown) so that the delivery catheter 80 (e.g., broncho-scope) can be retracted while the valve 50 is deployed in a predetermined location. A distal end of the delivery catheter 80 can extend out of a bronchoscope (not shown) and the anchor indicator 16 are aligned as shown by line (C).

Figures 2A, 2B:
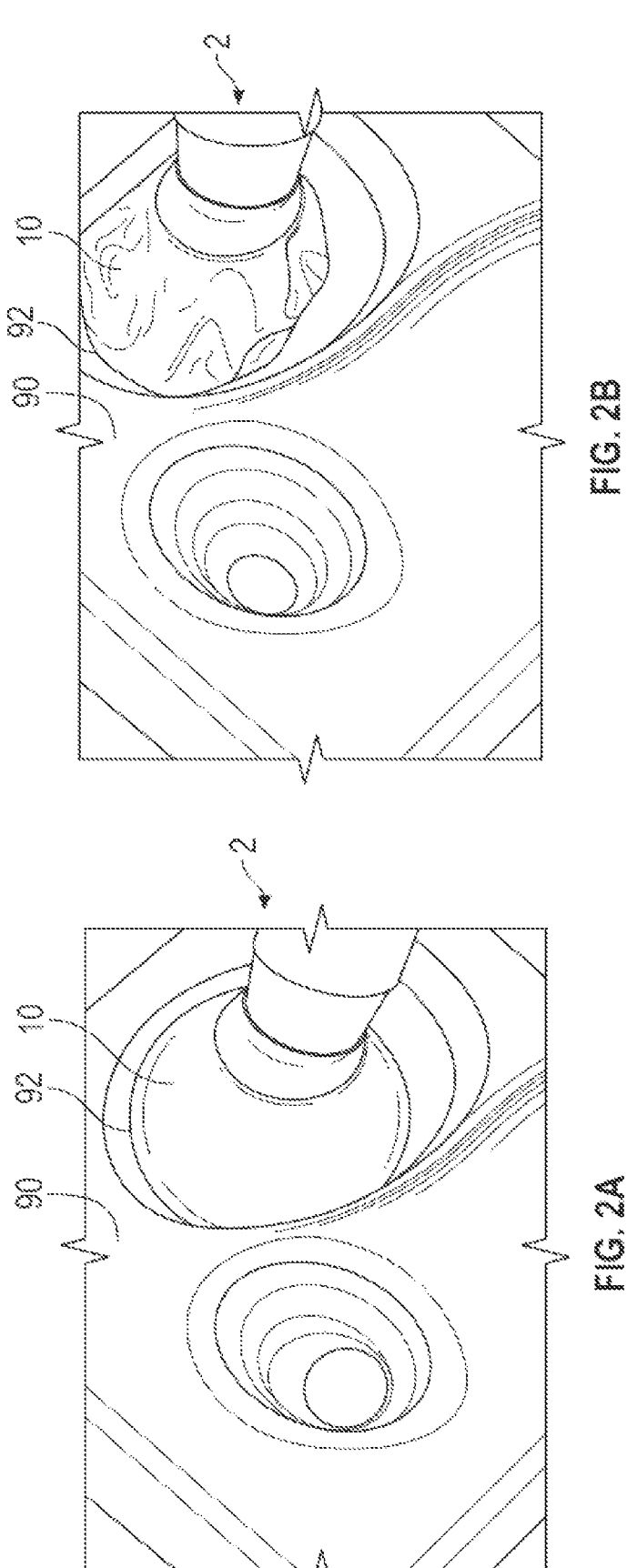
FIG. 2A illustrates the endoscopic view of an inserted balloon catheter inflated to a first pressure.
FIG. 2B illustrates the endoscopic view of an inserted balloon catheter at a neutral pressure.

FIG. 2A illustrates an inserted balloon catheter 2 inflated in a passageway 92 of a tissue 90 at a first pressure. The balloon 10 of balloon catheter 2 may be inflated to the first pressure in a passageway 92. When inflated to the first pressure, the balloon 10 may fill the passageway 92 so that the seal area indicator 12 of the balloon 10 is substantially in contact with a wall of the passageway 92. The seal area indicator 12 of balloon catheter 2 measures the passageway 92 such that the seal area indicator 12 indicates if the seal area 58 of the valve 50 in the deployed state 32 will seal the passage 92.

FIG. 2B illustrates an inserted balloon catheter 2 at a neutral pressure in a passageway 92 with no pressure applied to the balloon 10. The neutral pressure may be atmospheric pressure. As shown the balloon 10 still obstructs the view of the tangs 18. Accordingly, the balloon 10 of balloon catheter 2 may be deflated to a second pressure in a passageway 92. When deflated to the second pressure, the balloon 10 may reduce in size the passageway 92 so that the plurality of tangs 18 of anchor indicator 16 can be viewed. The plurality of tangs 18 of anchor indictor 16 of balloon catheter 2 indicate the area of the passageway 92 that will be contacted by the anchors 52 of the valve 50. The anchors 52 will be ensured to contact the walls of the passageway 92 if no additional passageway (not shown) is adjacent to the plu-rality of tangs 18 of anchor indicator 16. The tangs 18 represent the minimum size that the seal area 58 of the valve 50 can seal.

Figure 3C:
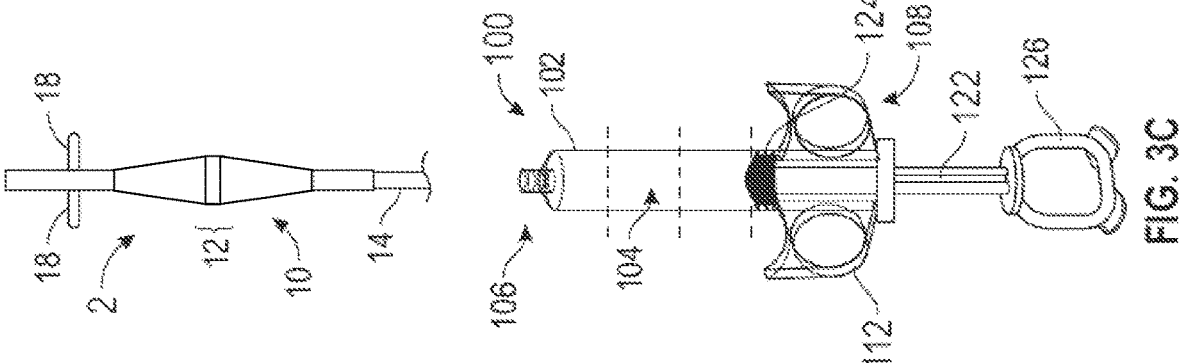
FIG. 3C illustrates a syringe and balloon catheter in a deflated state.
Figure 3B:
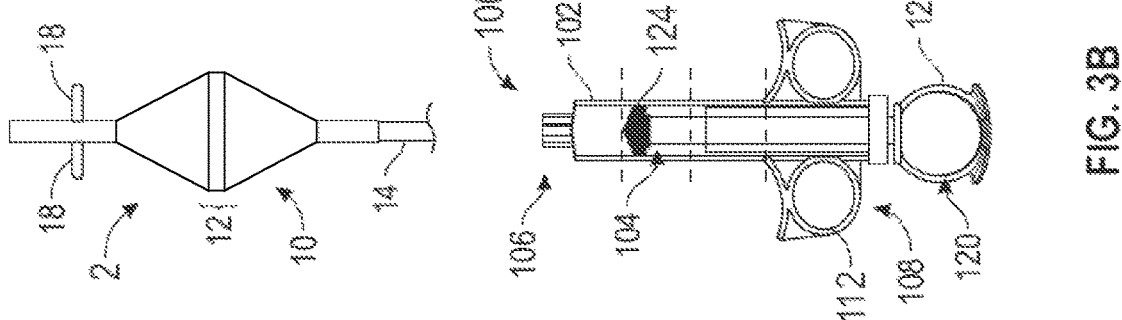
FIG. 3B illustrates a syringe and balloon catheter in an inflated state.
Figure 3A:
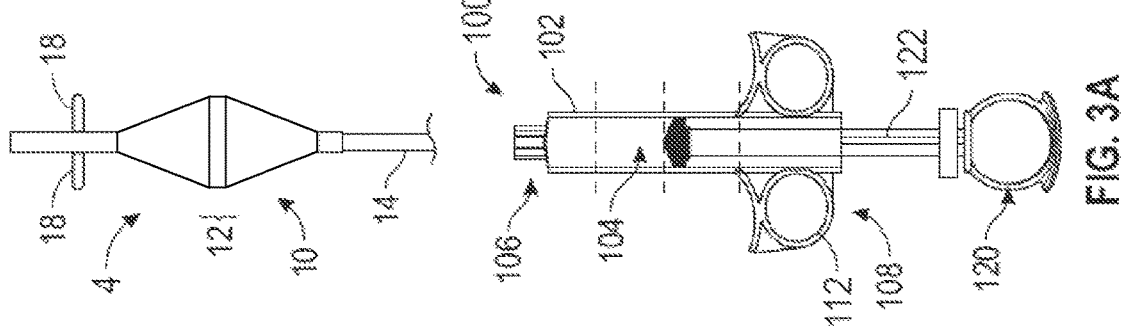
FIG. 3A illustrates a syringe and balloon catheter in a plunger starting position.

FIGS. 3A-3C illustrate a syringe 100 and the balloon catheter 2 in a plunger starting position (FIG. 3A), an inflated state (FIG. 3B), and a deflated state (FIG. 3C). The syringe 100 includes a channel portion 102 that defines a channel 104. The channel portion 102 has a distal end 106 and proximal end 108. The channel portion 102 may have a length, width, and/or volume such that the balloon 10 can be inflated without using all the fluid in the channel 104. The distal end 106 and proximal end 108 may be opposite each other. The distal end 106 may be positioned closer to the balloon catheter 2 and include a balloon catheter attachment component 110. The balloon catheter attachment component 110 may be configured to secure the balloon catheter 2 to the syringe 100. The proximal end 108 may be positioned closer to a user of the syringe 100. The proximal end 108 may be a free, open end of the channel portion 102. The proximal end 108 may include finger members 112. Finger members 112 may be shaped to receive fingers of a single hand of a user. The channel portion 102 may be sized to receive a plunger 120 through the free, open end of the channel portion 102 at the proximal end 108. The plunger 120 may include a stem 122, a plunger head 124, and a finger member 126. The stem 122 may extend between the plunger head 124 and the finger member 126. The stem 122 may have a length such that the plunger head 124 can be inserted into the channel 104 until the plunger head 124 abuts a distal end 106 of the channel portion 102. The plunger head 124 may be inserted into the channel 104, while the finger member 126 remains outside of the channel portion 102. The finger member 126 may be shaped to receive a finger of a single hand of a user. When the finger member 126 is used in combination with the finger members 112 of the channel portion 102, a user may be able to actuate the plunger 120 with respect to the channel portion 102. For example, a thumb of one hand of the user may be placed in or on the finger member 126 of the plunger 120, while a pointer finger and middle finger of the one hand into or onto the finger members 112 of the channel portion 102. Such positioning allows a force to be applied by a single hand of a user to actuate the plunger 120 in the channel 104.

The plunger head 124 may be sized to create a seal between the plunger head 124 and the channel portion 102, such that no fluid may pass from the distal end 106 to the proximal end 108 of the channel 104 through or by the plunger head 124. Accordingly, the plunger head 124, through actuation of the plunger 120 can expel fluid from the channel 104 into the balloon catheter 2 or withdraw fluid from the balloon catheter 2 into the channel 104.

For example, as shown in FIG. 3A, the plunger head 124 may be positioned at a plunger starting position (N) when the balloon catheter 2 is attached to the syringe 100. In the plunger starting position (N), the plunger head 124 may be partially inserted into the channel 104. The plunger starting position (N) may cause the balloon 10 of balloon catheter to be at a neutral position, such that the balloon 10 is neither inflated nor deflated. The plunger starting position (N) may cause the balloon 10 of balloon catheter 2 to be at a "zero" pressure. The plunger starting position (N) may cause the balloon 10 of balloon catheter 2 to be at atmospheric pressure. The plunger starting position (N) may be positioned approximately one third or one half of the length of the channel portion 102 from the proximal end 108 to the distal end 106.

For example, as shown in FIG. 3B, when the plunger head 124 is inserted further into the channel 104, the plunger head 124 may be positioned at an inflation position (I). The inflation position (I) is between the plunger starting position (N) and the distal end 108 of the channel portion 102. In moving the plunger head 124 to the inflated position (I), the actuation of the plunger 120 may cause liquid from channel 104 to travel into the balloon catheter 2. Such addition of fluid into the balloon catheter 2 may cause the balloon 2 reach an inflated state (e.g., a deployed state) with an inflation pressure. The inflated state may cause the balloon 10 to reach a maximum diameter at the seal area indicator 12. If the balloon 10 reaches the inflated state, and additional fluid is added to the balloon 10, the pressure in the balloon 10 may increase rapidly. In some embodiments, the inflation pressure is approximately fifteen to sixteen psi above atmospheric pressure. In some embodiments, the inflated position (I) is located at the distal end 106 of the channel portion 102, such that the plunger 120, and therefore plunger head 124, is fully inserted into the channel 104 to reach the inflated position (I).

For example, as shown in FIG. 3C, when the plunger head 124 is retracted within the channel 104, the plunger head 124 may be positioned at a deflation position (E). The deflation position (E) may be positioned between the plunger starting position (N) and the proximal end 108 of the channel portion 102. In moving the plunger head 124 to the deflated position (E), the actuation of the plunger 120 may cause liquid from balloon catheter 2, and therefore balloon 10, to travel into the channel 104 of the channel portion 102. Such removal of fluid from the balloon catheter 2 may cause the balloon to reach a deflated state, with a deflated pressure. The deflated state may reduce the diameter at the seal area indicator 12, allowing tangs 18 to be viewed. In some embodiments, the deflation pressure is approximately two to three psi below atmospheric pressure. In some embodiments, the deflated position (E) is located at the proximal end 108 of the channel portion 102, such that the plunger 120, and therefore plunger head 124, is fully retracted or withdrawn, while still within in the channel 104, to reach the deflated position (E).

Figure 4B:
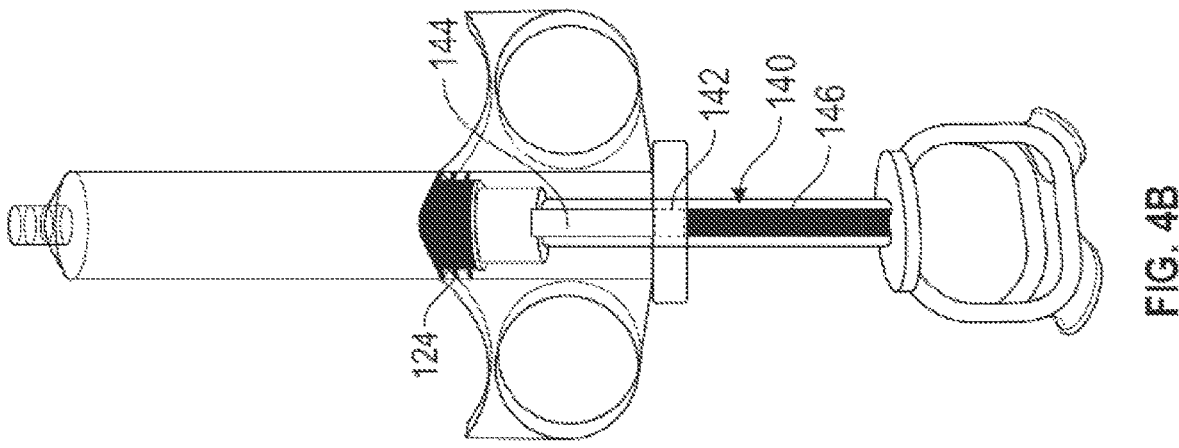
FIGS. 4A-4B illustrate example visual indicia on syringes as described herein, which may be used to aid in inflation or deflation of a balloon catheter.
Figure 4A:
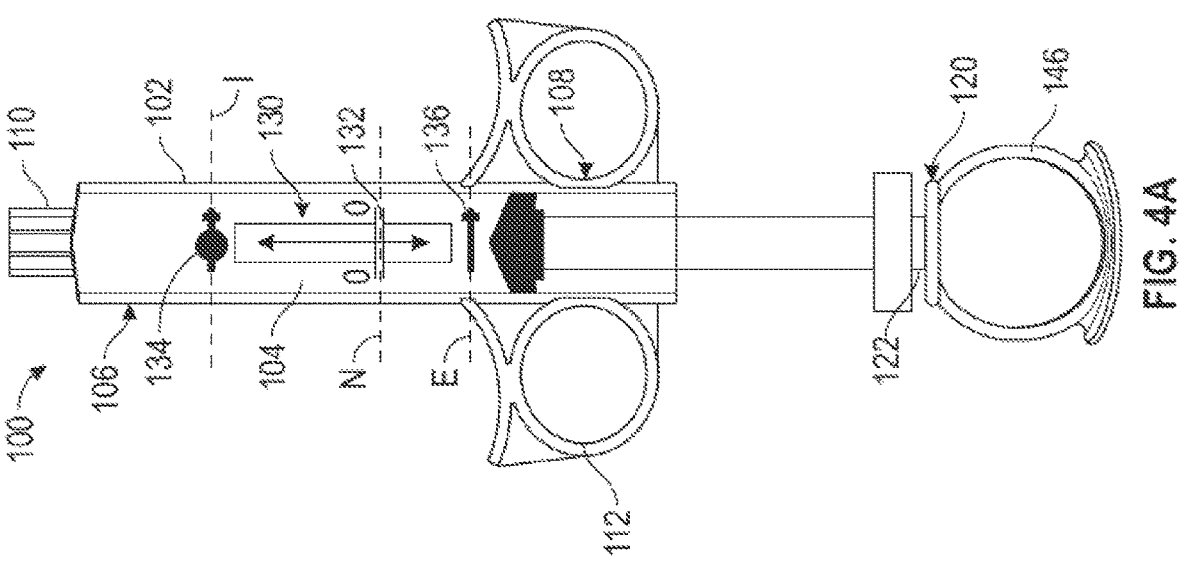

FIGS. 4A-4B illustrate example visual indicia 130 or 140 on syringe 100, which may be used to inflate or deflate the balloon 10 of balloon catheter 2.

The syringe 100 may include visual indicia 130 or 140 that may include a plunger starting position visual indicia 132 or 142, an inflation position visual indicia 134 or 144, and/or a deflation position visual indicia 136 or 146. The plunger head 124 may be moved in the channel 104 in either direction to allow the plunger head 124 to align with the plunger starting position visual indicia 132 or 142, the inflation position visual indicia 134 or 144, and/or deflation position visual indicia 136 or 146.

The plunger starting position visual indicia 132 or 142 may correspond to a mid-span "zero," a plunger starting location, or an initial or neutral pressure. The plunger starting position visual indicia 132 or 142 may be located at one half of the length of the channel portion 102. The plunger starting position visual indicia 132 or 142 may be located at one third of the length of the channel portion 102. The plunger starting position visual indicia 132 or 142 may cause the pressure in the balloon 10 to be atmospheric pressure. The inflation position visual indicia 134 or 144 may correspond to a plunger extension point, a plunger insertion point, or a inflation point. The inflation position visual indicia 134 or 144 may correspond to a nominal positive pressure to inflate the balloon 10. The inflation position visual indicia 134 or 144 can be located such that the plunger head 124 is fully inserted into the channel 104 to reach the inflation position visual indicia 134 or 144. In some embodiments, the stroke length between the plunger starting position visual indicia 132 or 142 and the inflation position visual indicia 134 or 144 results in a nominal positive pressure of the balloon 10 of about 15-16 pounds per square inch (psi). The deflation position visual indicia 136 or 146 may correspond to a nominal vacuum to deflate the balloon 10. In some embodiments, the balloon 10 deflates sufficiently to be pulled back into a working channel. In some embodiments, the balloon 10 deflates sufficiently to see distal of the balloon 10 to tangs 18. In some embodiments, the deflation position visual indicia 136 or 146 is located such that the plunger head 124 is fully withdrawn in the channel 104, without being removed from the channel 104, to reach the deflation position visual indicia 136 or 146. In some embodiments, the stroke length between the plunger starting position visual indicia 132 or 142 and the deflation position visual indicia 136 or 146 results in a nominal vacuum of about 2-3 psi.

As shown in FIG. 4A, the visual indicia 130 may be located on the channel portion 102 of the syringe 100. The channel portion 102 may be transparent or translucent, such that the plunger head 124 can be seen through the channel portion 102. The plunger head 124 may be black, white, or a color that contrasts with the visual indicia 130 on the channel portion 102. The plunger starting position visual indicia 132 may indicate the plunger starting position (N) with a line, with two parallel lines, with a "0", with a band of a designated color, with a symbol or marking, a block of color, or a combination thereof on the channel portion 102. The plunger starting position visual indicia 132 may contrast with the plunger head 124. The inflation position visual indicia 134 may indicate the inflation position (I) with a line, an arrowhead of an arrow, a symbol or marking (e.g., an inflated balloon, a plus sign, etc.), a block of color, or a combination thereof. The deflation position visual indicia 136 may indicate the deflation position (E) with a line, an arrowhead of an arrow, a symbol or marking (e.g., a deflated balloon, a minus sign, etc.), a block of color, or a combination thereof. A proximal end of the plunger head 124, a distal end of the plunger head 124, or a middle portion of the plunger head 124 may be aligned with the plunger starting position visual indicia 132, the inflation position visual indicia 134, and/or the deflation position visual indicia 136 to achieve the desired pressure. The visual indicia 130 may include additional coloring, markings, symbols, or a combination thereof between the plunger starting position visual indicia 132, the inflation position visual indicia 134, and/or the deflation position visual indicia 136.

As shown in FIG. 4B, the visual indicia 140 may be located on the stem 122 of the plunger 120 of the syringe 100. The plunger 120 can be moved so that visual indicia 140 align with an edge of the channel portion 102 at the different nominal strokes. The channel portion 102 may be transparent or translucent, such that the plunger head 124 and plunger stem 122 can be seen through the channel portion 102. The plunger head 124 may be black, white, or a color for ease of viewing when in the channel portion 102. The plunger starting position visual indicia 142 may indicate the plunger starting position (N) with a line, with two parallel lines, with a "0", with a band of a designated color, with a symbol or marking, a block of color, a dotted line or box, or a combination thereof on the plunger stem 122. The plunger starting position visual indicia 142 may contrast with the channel portion 102 and/or any coloring of the plunger stem 122. The inflation position visual indicia 144 may indicate the inflation position (I) with a line, an arrowhead of an arrow, a symbol or marking (e.g., an inflated balloon, a plus sign, etc.), a block of color, or a combination thereof. The deflation position visual indicia 146 may indicate the deflation position (E) with a line, an arrowhead of an arrow, a symbol or marking (e.g., a deflated balloon, a minus sign, etc.), a block of color, or a combination thereof. The combination of the plunger stem 122 and the proximal end of the channel portion 102 may be aligned with the plunger starting position visual indicia 132, the inflation position visual indicia 134, and/or the deflation position visual indicia 136 to achieve the desired pressure. The visual indicia 140 may include additional coloring, markings, symbols, or a combination thereof between the plunger starting position visual indicia 142, the inflation position visual indicia 144, and/or the deflation position visual indicia 146.

Figure 5:
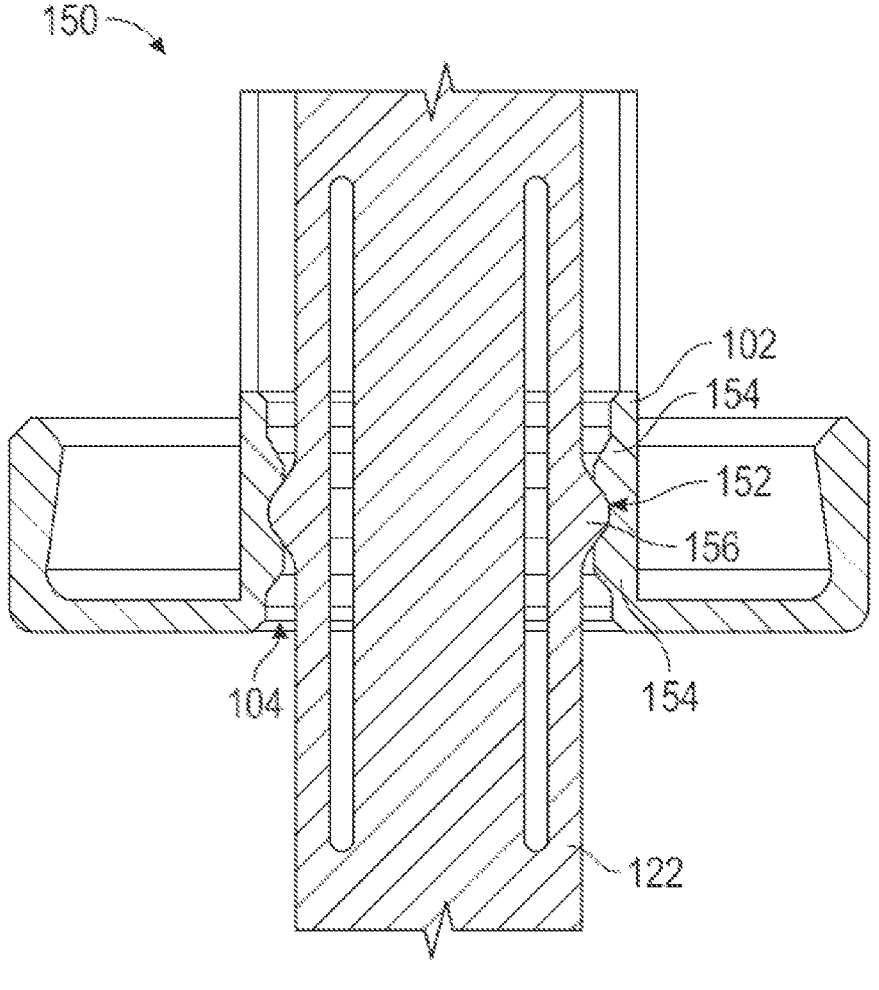
FIG. 5 illustrates components for tactile feedback of the syringe.

FIG. 5 illustrates components for tactile feedback when using the syringe 100. In some embodiments, the syringe 100 is designed to include a tactile feedback component 150 that indicates one or more of the plunger starting position (N), the inflated position (I), or the deflated position (E). This tactile feedback component 150 can include bumps 154 to an inner wall of the channel portion 102. The bumps 154 can define at least one groove 152 between the bumps 154. The tactile feedback component 150 can include one or more bumps 156 on the plunger stem 122. The one or more bumps 156 on the plunger stem 122 can correspond to the at least one groove 152. Therefore, the result of the plunger stem 122 bump 156 and corresponding groove 152 is that the bump 156 on the plunger 120 clicks into the groove 152 at the plunger starting position (N). The tactile feedback component 150, or a secondary tactile feedback component can be located at the inflated position (I) or the deflated position (E). The tactile feedback component 150 may result in a user-friendly force to disengage from the plunger starting position (N) in either direction. The tactile feedback component 150 can facilitate one-handed operation of the syringe 100.

Figure 6:
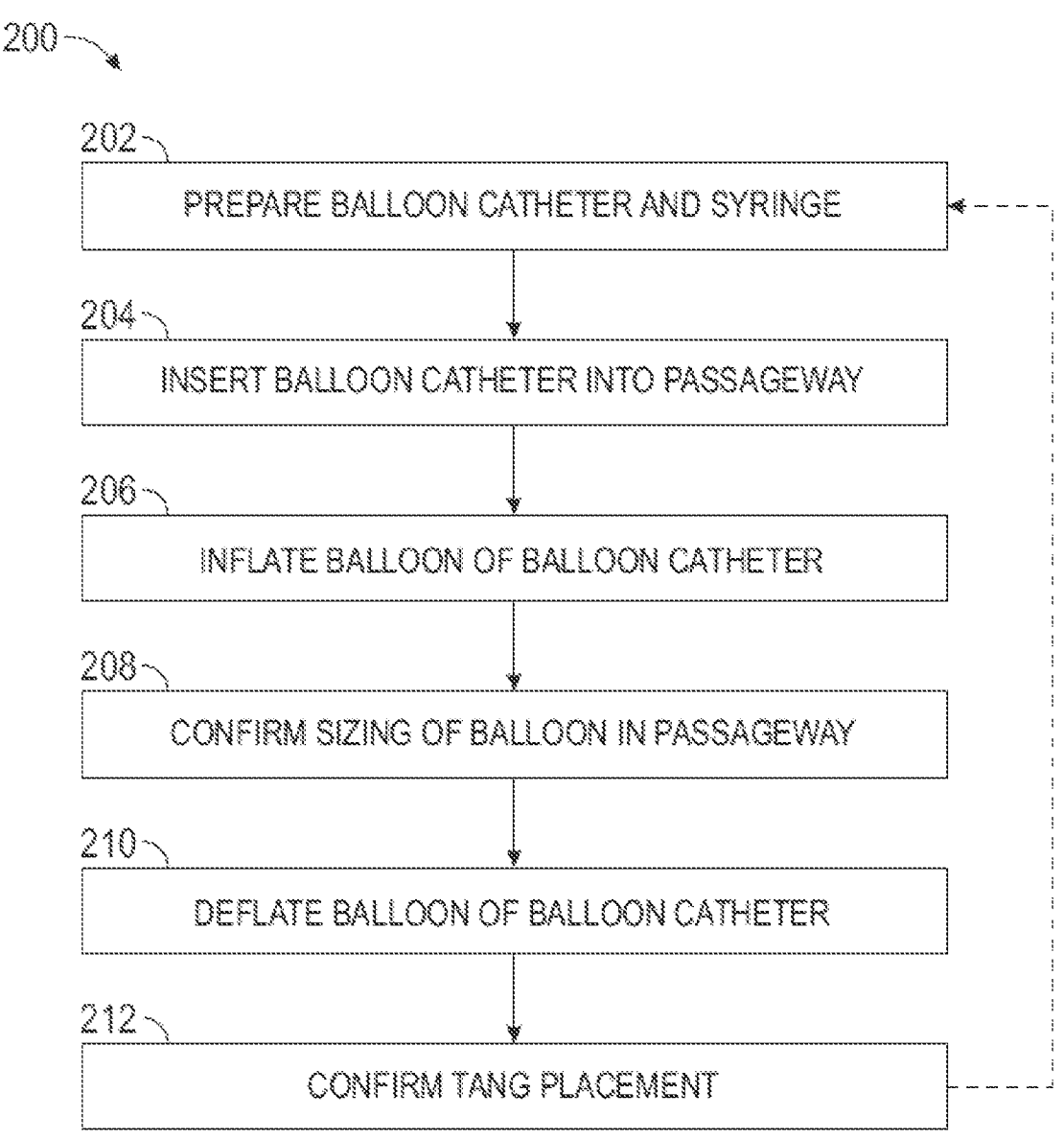
FIG. 6 shows an example of portions of a method of using a balloon catheter and syringe.

FIG. 6 shows an example of portions of a method of using a balloon catheter and syringe. The balloon catheter and syringe may be used in a method 200 that may employ one or more of the acts herein that may be employed in virtually any order. Method 200 may be employed to size a passageway. At 202, the balloon catheter and syringe may be prepared. Preparing the balloon catheter and syringe may include loading a balloon catheter in a delivery catheter or a bronchoscope. Preparing the balloon catheter and syringe may include attaching the balloon catheter to the syringe. Preparing the balloon catheter and syringe may include attaching the balloon catheter to the syringe when the plunger head of the syringe is located at a plunger starting position. At 204, the balloon catheter may be inserted into the passageway of a patient. Inserting the balloon catheter may include retracting the balloon catheter to position the balloon catheter. Inserting the balloon catheter may include inserting a delivery catheter into a passageway. Inserting the balloon catheter may include retracting the delivery catheter to expose a balloon on the balloon catheter. Inserting the balloon catheter may include moving the balloon catheter into the passageway to be sealed by a valve. At 206, the balloon of the balloon catheter may be inflated. Inflating the balloon of the balloon catheter may include moving the plunger further into the channel of the syringe. Moving the plunger further into the channel may include moving the plunger until the plunger head reaches an inflation visual indicia (e.g., on the syringe channel portion or on the stem of the plunger). At 208, the size of the balloon in comparison to the passage may be confirmed. Confirming sizing of the balloon in the passageway may include a visual inspection of the balloon. Visual inspection of the balloon may include moving an imaging device around the outside of the balloon catheter or delivery catheter to inspect a seal area of the balloon. Confirming sizing of the balloon in the passageway may also include a tactile inspection of the balloon. Tactile inspection may include inserting and retracting the balloon across the passageway while observing the forces on the balloon catheter. The visual inspection and tactile inspection may be performed when the balloon is fully inflated or while the balloon is being inflated. The visual inspection may compare the balloon on the balloon catheter to the structure to determine if the valve can seal the structure (i.e., passageway). The tactile inspection may compare forces on the balloon catheter while the balloon is inflated to forces on the balloon catheter while the balloon is not inflated to determine if the valve can seal the structure. At 210, the balloon of the balloon catheter may be deflated. Deflating the balloon of the balloon catheter may include moving the plunger head closer to a free, open end of the channel portion of the syringe. Deflating the balloon may include moving the plunger until the plunger head reaches a deflation visual indicia (e.g., on the syringe channel portion or on the stem of the plunger). At 212, the tang placement of the balloon catheter may be confirmed. Confirming tang placement may include a visual inspection of the tangs. The visual inspection may be performed when the tangs are being inserted. The visual inspection may be performed during deflation of the balloon or when the balloon is fully deflated. Method 200 may include visually inspecting the balloon, the tangs, the seal area indicator, or a combination thereof. Method 200 may include determining the size of the valve by using a valve that is substantially similar in size to the balloon on the balloon catheter when the balloon is fully inflated. Method 200 may include removing the balloon catheter from the passageway and the patient. Method 200 may include inserting a second balloon catheter or a third balloon catheter into the passageway and repeating the acts taught herein. Inserting a second balloon catheter or a third balloon catheter into the passageway and repeating the acts taught may include using the same syringe, with the same visual indicia locations, for the second balloon catheter and/or the third balloon catheter, even if the size of the balloon on the second or third balloon catheter is different than the size of the balloon on the first balloon catheter.

A kit may include one or more of the balloon catheters and syringes of the teachings herein. The kit may include one or more valves. The kit may include one balloon catheter for each of the valves that may be used. The kit may include a measuring device. The kit may include two or more balloon catheter, three or more balloon catheter, or four or more balloon catheter. The kit may include an instructions manual. When the kit includes more than one balloon catheter the balloon on the balloon catheter may be a different size. The different size balloons may have a different outer diameter. The kit may include the same number of balloon catheters as there are available valve sizes. The syringe may be able to inflate and deflate all the balloons of the multiple balloon catheters. The syringe may be able to inflate and deflate all the balloons of the multiple balloon catheters by injecting or withdrawing the same amount of fluid to each balloon catheter. The syringe may include visual indicia identifying a plunger starting position, an inflation position, and a deflation position. The plunger starting position, an inflation position, and a deflation position may be the same for all the balloons of the multiple balloon catheters.

Each of the following non-limiting examples may stand on its own, or may be combined in various permutations or combinations with one or more of the other examples.

Example 1 is a syringe for inflating a balloon catheter, the syringe comprising: a channel portion shaped to create a channel, the channel portion including at least one visual indicia indicating a plunger starting position, the plunger starting position located between a balloon catheter insertion end and a plunger receiving end; a plunger, including an inserted end and a free end, which when positioned in the channel at the plunger starting position, causes a starting pressure to be applied to the balloon catheter; and wherein when the plunger is inserted in the channel between the plunger starting position and the balloon catheter insertion end an inflation pressure for the syringe above the starting pressure is applied to the balloon catheter and when the plunger is retracted from the channel between the plunger starting position and the plunger receiving end, a deflation pressure for the syringe below the starting pressure is applied to the balloon catheter.

In Example 2, the subject matter of Example 1 includes, wherein the starting pressure is atmospheric pressure.

In Example 3, the subject matter of Examples 1-2 includes, wherein the plunger starting position is approximately one third or one half of a length of the channel portion from the plunger receiving end to the balloon catheter insertion end In Example 4, the subject matter of Examples 1-3 includes, wherein the at least one visual indicia is located on a transparent or translucent portion of an outer surface of the channel portion and wherein the plunger includes a color at the inserted end, wherein the color is visible when the plunger is inserted into the channel.

In Example 5, the subject matter of Examples 1~4 includes, wherein an inner surface of the channel portion includes a groove and wherein an outer surface of the plunger includes a raised bump configured to fit in the groove.

In Example 6, the subject matter of Example 5 includes, wherein the groove and raised bump align the plunger with the plunger starting position.

In Example 7, the subject matter of Examples 1-6 includes, wherein the free end is configured to receive a force applied by a single hand of a user to advance the plunger within the channel.

In Example 8, the subject matter of Examples 1-7 includes, wherein when the plunger is inserted into the channel proximal the balloon catheter insertion end from the plunger starting position to an inflation position, fluid is pushed into the balloon catheter, causing a balloon on the balloon catheter to inflate to the inflation pressure.

In Example 9, the subject matter of Example 8 includes, wherein the inflation pressure is approximately fifteen to sixteen psi above atmospheric pressure.

In Example 10, the subject matter of Examples 8-9 includes, wherein a volume within the channel between the plunger starting position and the inflation position corresponds to a full inflation volume of a non-compliant balloon for sizing an inner lateral dimension of a location of a pulmonary passage for locating a selected size checkvalve at the location.

In Example 11, the subject matter of Examples 8-10 includes, wherein the inflation position is when the plunger is fully inserted in the channel.

In Example 12, the subject matter of Examples 1-11 includes, wherein when the plunger is withdrawn in the channel proximal the plunger receiving end from the plunger starting position to a deflation position, fluid is removed from the balloon catheter, causing a balloon on the balloon catheter to deflate to the deflation pressure.

In Example 13, the subject matter of Example 12 includes, wherein the deflation pressure is approximately two to three psi below atmospheric pressure.

In Example 14, the subject matter of Examples 12-13 includes, wherein a volume within the channel between the plunger starting position and the deflation position corresponds to a deflation volume of a non-compliant balloon for confirming tang placement in a location of a pulmonary passage for a checkvalve at the location.

In Example 15, the subject matter of Examples 12-14 includes, wherein the deflation position is when the plunger is fully retracted in the channel.

Example 16 is a method for using a syringe to inflate a balloon catheter, the method comprising: affixing the syringe to the balloon catheter while a plunger of the syringe is partially inserted in a channel portion of the syringe, the partial insertion corresponding to an insertion end of the plunger being at a plunger starting position causing a balloon of the balloon catheter to be inflated to a starting pressure, wherein the plunger starting position is identifiable by a visual indicia on the channel portion; inserting the balloon catheter to a target location within a patient airway; and applying a force to the plunger to move the plunger further into the channel portion including moving the insertion end proximal to the balloon catheter to an inflation position to cause the balloon of the balloon catheter to inflate to an inflation pressure.

In Example 17, the subject matter of Example 16 includes, wherein when the plunger is moved further into the channel portion proximal to the balloon catheter from the plunger starting position to the inflation position, fluid is pushed into the balloon catheter.

In Example 18, the subject matter of Examples 16-17 includes, wherein the inflation pressure is approximately fifteen to sixteen psi above atmospheric pressure.

In Example 19, the subject matter of Examples 16-18 includes, further comprising sizing an inner lateral dimension of a location of a pulmonary passage for locating a selected size checkvalve at the location by verifying a fit of the balloon when at the inflation pressure at the location, wherein a volume within the channel between the plunger starting position and the inflation position corresponds to a full inflation volume of a non-compliant balloon.

In Example 20, the subject matter of Examples 16-19 includes, wherein applying the force to the plunger to move the plunger further into the channel portion including moving the insertion end proximal the balloon catheter to the inflation position comprises applying force to the plunger to move the plunger fully into the channel portion.

In Example 21, the subject matter of Examples 16-20 includes, further comprising applying a force to the plunger to withdraw the plunger in the channel portion including moving the insertion end distal to the balloon catheter to a deflation position to cause the balloon of the balloon catheter to deflate to a deflation pressure.

In Example 22, the subject matter of Example 21 includes, wherein when the plunger is withdrawn in the channel portion distal to the balloon catheter to the deflation position, fluid is removed from the balloon catheter.

In Example 23, the subject matter of Examples 21-22 includes, wherein the deflation pressure is approximately two to three psi below atmospheric pressure.

In Example 24, the subject matter of Examples 21-23 includes, further comprising confirming tang placement in a location of a pulmonary passage for a checkvalve at the location by verifying tang placement of tangs of the balloon catheter when at the deflation pressure at the location, wherein a volume within the channel between the plunger starting position and the deflation position corresponds to a deflation volume of a non-compliant balloon.

In Example 25, the subject matter of Examples 21-24 includes, wherein applying the force to the plunger to withdraw the plunger in the channel portion including moving the insertion end distal to the balloon catheter to the deflation position comprises applying force to the plunger to move the plunger to a most distal end of the channel portion.

In Example 26, the subject matter of Examples 16-25 includes, wherein the starting pressure is atmospheric pressure.

In Example 27, the subject matter of Examples 16-26 includes, wherein the plunger starting position is approximately one third or one half of a length of the channel portion.

In Example 28, the subject matter of Examples 16-27 includes, wherein the at least one visual indicia is located on a transparent or translucent portion of an outer surface of the channel portion and wherein the plunger includes a color at the insertion end, wherein the color is visible when the plunger is inserted into the channel portion.

In Example 29, the subject matter of Examples 16-28 includes, wherein applying a force to the plunger to move the plunger within the channel portion comprises applying a force to dislodge a raised bump of an outer surface of the plunger from a groove of the inner surface of the channel portion, wherein the raised bump is configured to fit in the groove.

In Example 30, the subject matter of Example 29 includes, wherein the groove and raised bump align the plunger with the plunger starting position.

In Example 31, the subject matter of Examples 16-30 includes, wherein applying the force to the plunger comprises using a single hand to apply the force to move the plunger.

Example 32 is a kit comprising: at least two balloon catheters with balloons of different sized maximum outer diameters; and a syringe including: a channel portion shaped to create a channel; a plunger, including an inserted end and a free end, which when positioned in the channel at the plunger starting position, causes a starting pressure to be applied to the balloon catheter; and wherein the channel portion or the plunger includes at least one visual indicia indicating the plunger starting position, the plunger starting position located along an insertion axis.

In Example 33, the subject matter of Example 32 includes, wherein the starting pressure is atmospheric pressure.

In Example 34, the subject matter of Examples 32-33 includes, wherein the plunger starting position is approximately one third or one half of a length of the channel portion from a plunger receiving end to a balloon catheter insertion end of the channel portion.

In Example 35, the subject matter of Examples 32-34 includes, wherein the at least one visual indicia is located on a transparent or translucent portion of an outer surface of the channel portion and wherein the plunger includes a color at the inserted end, wherein the color is visible when the plunger is inserted into the channel.

In Example 36, the subject matter of Examples 32-35 includes, wherein an inner surface of the channel portion includes a groove and wherein an outer surface of the plunger includes a raised bump configured to fit in the groove.

In Example 37, the subject matter of Examples 36 includes, wherein the groove and raised bump align the plunger with the plunger starting position.

In Example 38, the subject matter of Examples 32-37 includes, wherein the free end is configured to receive a force applied by a single hand of a user to advance the plunger within the channel.

In Example 39, the subject matter of Examples 32-38 includes, wherein when the plunger is inserted into the channel proximal to the balloon catheter from the plunger starting position to an inflation position, fluid is pushed into the balloon catheter, causing a balloon on the balloon catheter to inflate to an inflation pressure.

In Example 40, the subject matter of Example 39 includes, wherein the inflation position is positioned to be able to inflate either of the balloons of different sized maximum outer diameters that is attached to the syringe.

In Example 41, the subject matter of Examples 39-40 includes, wherein the inflation pressure is approximately fifteen to sixteen psi above atmospheric pressure.

In Example 42, the subject matter of Examples 39-41 includes, wherein a volume within the channel between the plunger starting position and the inflation position corresponds to a full inflation volume of one of the balloons, wherein the balloons are a non-compliant balloon for sizing an inner lateral dimension of a location of a pulmonary passage for locating a selected size checkvalve at the location.

In Example 43, the subject matter of Examples 39-42 includes, wherein the inflation position is located in a position where the plunger is fully inserted in the channel.

In Example 44, the subject matter of Examples 32-43 includes, wherein when the plunger is withdrawn in the channel distal to the balloon catheter from the plunger starting position to a deflation position, fluid is removed from the balloon catheter, causing a balloon on the balloon catheter to deflate to the deflation pressure.

In Example 45, the subject matter of Example 44 includes, wherein the deflation pressure is approximately two to three psi below atmospheric pressure.

In Example 46, the subject matter of Examples 44-45 includes, wherein a volume within the channel between the plunger starting position and the deflation position corresponds to a deflation volume of the balloons, wherein the balloons are a non-compliant balloon for confirming tang placement in a location of a pulmonary passage for a checkvalve at the location.

In Example 47, the subject matter of Examples 44-46 includes, wherein the deflation position is located at a position where the plunger is fully retracted in the channel.

Example 48 is a syringe for inflating a balloon catheter, the syringe comprising: a channel portion shaped to create a channel; a plunger, including an inserted end and a free end, the plunger including at least one visual indicia indicating a location of zero applied pressure, the location of zero applied pressure located between the inserted end and the free end, and wherein when the plunger is inserted in the channel to place the inserted end at the location of zero applied pressure, atmospheric pressure is caused to be applied to the balloon catheter; and wherein when the plunger is fully inserted in the channel a maximum pressure for the syringe above atmospheric pressure is applied to the balloon catheter and when the plunger is fully retracted from the channel a minimum pressure for the syringe below atmospheric pressure is applied to the balloon catheter.

In Example 49, the subject matter of Example 48 includes any of Examples 1-15.

Example 50 is a syringe device for inflating a non-compliant balloon for sizing an inner lateral dimension of a location of a pulmonary passage for locating a selected size checkvalve at the location, the device comprising: a channel portion shaped to create a channel, the channel portion including at least one visual indicia indicating a plunger starting position, the plunger starting position located between a balloon catheter insertion end and a plunger receiving end, the channel also including a user-discernable plunger stopping location; a plunger, including an inserted end inserted in the channel to place the inserted end at the plunger starting position; and wherein when the plunger is moved from the plunger starting position to the plunger stopping location, the non-compliant balloon is expanded to its maximum outer diameter for sizing the inner lateral dimension of the location of the pulmonary passage.

In Example 51, the subject matter of Example 50 includes any of Examples 1-15.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A syringe for inflating a balloon catheter, the syringe comprising:

a channel portion including a balloon catheter insertion end and a plunger receiving end, the channel portion shaped to create a channel, the channel portion including a groove at a plunger starting position located between the balloon catheter insertion end and the plunger receiving end;

a plunger, including an inserted end and a free end; and an outer surface of the inserted end of the plunger includes a raised bump corresponding with the groove such that the outer surface of the of the inserted end of the plunger locks into the channel portion at the plunger starting position and maintains an atmospheric pressure within the balloon catheter;

wherein when the plunger is advanced in the channel from the plunger starting position toward the balloon catheter insertion end an inflation pressure for the syringe above the atmospheric pressure is applied to the balloon catheter and when the plunger is retracted in the channel from the plunger starting position toward the plunger receiving end, a deflation pressure for the syringe below the atmospheric pressure is applied to the balloon catheter.

2. The syringe of claim 1, wherein the plunger starting position is approximately one third or one half of a length of the channel portion from the plunger receiving end to the balloon catheter insertion end.

3. The syringe of claim 1, further comprising at least one visual indicia located on a transparent or translucent portion of an outer surface of the channel portion and wherein the plunger includes a color at the inserted end, wherein the color is visible when the plunger is inserted into the channel.

4. The syringe of claim 1, wherein the groove and raised bump align the plunger with the plunger starting position.

5. The syringe of claim 1, wherein the free end is configured to receive a force applied by a single hand of a user to advance the plunger within the channel.

6. The syringe of claim 1, wherein when the plunger is advanced into the channel proximal the balloon catheter insertion end from the plunger starting position to an inflation position, fluid is pushed into the balloon catheter, causing a balloon on the balloon catheter to inflate to the inflation pressure.

7. The syringe of claim 6, wherein the inflation pressure is approximately fifteen to sixteen psi above atmospheric pressure.

8. The syringe of claim 6, wherein a volume within the channel between the plunger starting position and the inflation position corresponds to a full inflation volume of a non-compliant balloon for sizing an inner lateral dimension of a location of a pulmonary passage for locating a selected size checkvalve at the location.

9. The syringe of claim 6, wherein the inflation position indicates that the inflation pressure is maintained within the balloon catheter.

10. The syringe of claim 1, wherein when the plunger is withdrawn from the channel proximal the plunger receiving end from the plunger starting position to a deflation position, fluid is removed from the balloon catheter, causing a balloon on the balloon catheter to deflate to the deflation pressure.

11. The syringe of claim 10, wherein the deflation pressure is approximately two to three psi below atmospheric pressure.

12. The syringe of claim 10, wherein a volume within the channel between the plunger starting position and the deflation position corresponds to a deflation volume of a non-compliant balloon for confirming tang placement in a location of a pulmonary passage for a checkvalve at the location.

13. The syringe of claim 10, wherein the deflation position indicates that the deflation pressure is maintained within the balloon catheter.

14. A method for using a syringe to inflate a balloon catheter, the method comprising:

affixing the syringe to the balloon catheter, wherein the syringe includes:

a plunger, including an inserted end and a free end; and a channel portion, the channel portion including a balloon catheter insertion end and a plunger receiving end, the channel portion shaped to create a channel:

inserting the inserted end of the plunger into the channel created by the channel portion;

locking a raised bump located on an outer surface of the inserted end of the plunger into a groove located on the channel portion at a plunger starting position located between the balloon catheter insertion end and the plunger receiving end to maintain an atmospheric pressure within the balloon catheter;

inserting the balloon catheter to a target location within a patient airway; and applying a force to the plunger to move the plunger further into the channel portion including moving the insertion end to an inflation position to cause the balloon of the balloon catheter to inflate to an inflation pressure.

15. The method of claim 14, wherein the channel portion includes at least one visual indicia located on a transparent or translucent portion of an outer surface of the channel portion and wherein the plunger includes a color at the inserted end, wherein the color is visible when the plunger is inserted into the channel portion.

16. A kit comprising:

at least two balloon catheters with balloons of different sized maximum outer diameters; and a syringe including:

a channel portion including a balloon catheter insertion end and a plunger receiving end, the channel portion shaped to create a channel and further including a groove at a plunger starting position located between the balloon catheter insertion end and the plunger receiving end;

a plunger, including an inserted end and a free end; and an outer surface of the inserted end of the plunger including a raised bump corresponding with the groove such that the outer surface of the inserted end of the plunger locks into the channel portion at the plunger starting position and maintains an atmospheric pressure within the at least two balloon catheters; and wherein when the plunger is advanced in the channel from the plunger starting position toward the balloon catheter insertion end an inflation pressure for the syringe above the atmospheric pressure is applied to the at least two balloon catheters and when the plunger is retracted in the channel from the plunger starting position toward the plunger receiving end, a deflation pressure for the syringe below the atmospheric pressure is applied to the at least two balloon catheters.

17. The kit of claim 16, wherein at least one visual indicia is located on a transparent or translucent portion of the outer surface of the channel portion and wherein the plunger includes a color at the inserted end, wherein the color is visible when the plunger is inserted into the channel.

18. The kit of claim 16, wherein when the plunger is inserted into the channel proximal to the balloon catheters from the plunger starting position to an inflation position, fluid is pushed into the balloon catheter, causing a balloon on the balloon catheter to inflate to an inflation pressure, wherein the inflation position is positioned to be able to inflate either of the balloons of different sized maximum outer diameters that is attached to the syringe.

* * * * *